(12) United States Patent
Thomas et al.

(10) Patent No.: US 9,404,906 B2
(45) Date of Patent: Aug. 2, 2016

(54) UNDERWATER VEHICLE AND SENSOR

(71) Applicants: David Glynn Thomas, Perth (AU);
Christopher John Kalli, Perth (AU);
Eric Randal Stine, Vallejo, CA (US)

(72) Inventors: David Glynn Thomas, Perth (AU);
Christopher John Kalli, Perth (AU);
Eric Randal Stine, Vallejo, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 29 days.

(21) Appl. No.: 14/564,260

(22) Filed: Dec. 9, 2014

(65) Prior Publication Data
US 2015/0177212 A1    Jun. 25, 2015

Related U.S. Application Data

(60) Provisional application No. 61/918,410, filed on Dec. 19, 2013.

(51) Int. Cl.
| | | |
|---|---|---|
| G01C 13/00 | (2006.01) | |
| G01N 33/18 | (2006.01) | |
| B63G 8/00 | (2006.01) | |
| B63G 8/08 | (2006.01) | |
| B63G 8/14 | (2006.01) | |
| G01N 1/12 | (2006.01) | |
| E02D 1/00 | (2006.01) | |

(Continued)

(52) U.S. Cl.
CPC ............ *G01N 33/1826* (2013.01); *B63G 8/001* (2013.01); *B63G 8/08* (2013.01); *B63G 8/14* (2013.01); *E02D 1/00* (2013.01); *G01C 13/00* (2013.01); *G01N 1/12* (2013.01); *G01N 1/14* (2013.01); *G01N 1/16* (2013.01); *G01N 33/1886* (2013.01); *G01N 33/1893* (2013.01); *B63G 2008/004* (2013.01); *B63G 2008/005* (2013.01)

(58) Field of Classification Search
None
See application file for complete search history.

(56) References Cited

U.S. PATENT DOCUMENTS

| | | |
|---|---|---|
| 3,795,810 A | 3/1974 | Belden et al. |
| 4,002,066 A * | 1/1977 | Ratigan ............... G01N 1/12 422/50 |

(Continued)

FOREIGN PATENT DOCUMENTS

| | | |
|---|---|---|
| EP | 0510951 | 10/1992 |
| WO | 2011017734 | 2/2011 |

OTHER PUBLICATIONS

Magnetic microsphere-confined graphene for the extraction of polycyclic aromatic hydrocarbons from environmental water samples coupled with high performance liquid chromatography-fluorescence analysis; Wang Weina; Ma Ruiyang; Wu Qiuhua; Wang Chun; Wang Zhi; Journal of Chromatography. 1293, pp. 20-27. (2013).

(Continued)

*Primary Examiner* — Andre Allen
(74) *Attorney, Agent, or Firm* — Freehills; Frank C. Turner

(57) ABSTRACT

Described herein is an underwater vehicle having a vehicle body with a buoyancy controller adapted to vary the buoyancy of the vehicle in order to control motion of the vehicle through an underwater environment. The vehicle further includes a sampling system and a sensor arrangement. The sampling system is adapted to sequentially sample fluid from the underwater environment at specified sampling times resulting in a sample sequence, each sample associated with a sample time and a fluid flow rate. The sensor arrangement includes a plurality of molecule sensors adapted to sense organic molecules in each respective sample of the sample sequence.

12 Claims, 5 Drawing Sheets

(51) Int. Cl.
*G01N 1/14* (2006.01)
*G01N 1/16* (2006.01)

(56) References Cited

U.S. PATENT DOCUMENTS

| | | | |
|---|---|---|---|
| 4,287,763 A * | 9/1981 | Richard | G01N 1/405 73/170.29 |
| 4,792,526 A | 12/1988 | Ouellette et al. | |
| 5,219,390 A * | 6/1993 | McClane | B01L 9/00 206/456 |
| 5,869,756 A * | 2/1999 | Doherty | B63B 22/18 405/188 |
| 6,035,705 A | 3/2000 | Alexander | |
| 6,536,272 B1 * | 3/2003 | Houston | G01N 1/12 702/2 |
| 6,978,688 B2 | 12/2005 | Engebretson | |
| 8,381,672 B1 | 2/2013 | Eriksen | |
| 2005/0120778 A1 * | 6/2005 | Von Herzen | G01N 33/18 73/61.41 |
| 2005/0148091 A1 * | 7/2005 | Kitaguchi | B01L 3/502715 436/164 |
| 2005/0226777 A1 * | 10/2005 | Bowers | G01N 1/14 422/501 |
| 2009/0007704 A1 * | 1/2009 | Bowers | G01N 1/14 73/864.34 |
| 2011/0214500 A1 * | 9/2011 | Cabrera | G01C 13/00 73/170.29 |
| 2012/0105830 A1 | 5/2012 | Pierce, Jr. et al. | |
| 2013/0068011 A1 * | 3/2013 | Van Mooy | G01N 1/10 73/170.29 |

OTHER PUBLICATIONS

Application of sulfur microparticles for solid-phase extraction of polycyclic aromatic hydrocarbons from sea water and wastewater samples; Khalili-Fard Vahid; Ghanemi Kamal; Nikpour Yadollah; Fallah-Mehrjardi Mehdi; Analytica Chimica Acta. 714, pp. 89-97. (2012).

Breier, J.A. et al, "A suspended-particle rosette multi-sampler for discrete biogeochemical sampling in low-particle-density waters," Deep Sea Research, Part 1. Oceanographic Reserch Papers, Pergamon Press, Oxford, GB, vol. 56, No. 9, Sep. 1, 2009, pp. 1579-1589, XP026281640, ISSN: 0967-0637, DOI: 10.1016/J.DSR. 2009.04.005.

International Search Report and the Written Opinion of the International Searching Authority, or the Declaration; International Application No. PCT/US2014/069216; dated Jul. 21, 2015.

* cited by examiner

UNDERWATER VEHICLE AND SENSOR

FIELD OF THE INVENTION

The invention relates to the field of hydrocarbon detection, and particularly to a sampling system and sensor for detecting organic molecules such as hydrocarbons, which may be used with an underwater vehicle. This application claims priority to U.S. Provisional Patent Application No. 61/918,410 filed Dec. 19, 2013, which is fully incorporated herein by reference.

BACKGROUND OF THE INVENTION

Various techniques can be used to collect data relating to underwater hydrocarbon reserves (e.g., to detect the presence of naturally occurring seafloor seepage) or relating to underwater infrastructure transporting fluid that contains hydrocarbons (e.g., to assess pipeline integrity). Reflection seismology or non-seismic detection technologies such as magnetometers are typically used. More specifically for a marine environment, satellite and airborne imaging, or shipborne multibeam imaging together with drop core sampling are often used.

To gather data closer to the seabed, tethered or untethered remotely operated underwater vehicles (ROVs) can be used. These vehicles are typically expensive and require extensive surface support. Conventional ocean gliders are able to glide at a depth of up to 1000 m to gather hydrocarbon data, and thus are limited to gathering data at relatively shallow depths. Furthermore, although fluorometer-type sensors for Polycyclic Aromatic Hydrocarbons (PAH) have been proposed for use with gliders, these sensors are often too large and consume too much power to be integrated into conventional gliders.

As described above, existing approaches are typically costly, and have a number of other limitations. Therefore it would be useful to have an alternative underwater system and/or method for gathering hydrocarbon data.

SUMMARY OF THE INVENTION

Described herein is the use of an autonomous underwater vehicle (AUV) and a sensor arrangement used for sensing organic molecules such as hydrocarbons in a sequence of fluid samples.

In one aspect of the invention there is provided a sensor comprising: i) a sensing unit comprising: a cartridge having a sequence of slots, and a molecule sensor in each slot for sensing organic molecules; and ii) a sampling system adapted to sequentially sample fluid from an underwater environment at specified sampling times, the sampling system comprising: a fluid inlet on an upstream side of the sensing unit, and a valve system adapted to open and close successive slots in the cartridge to provide fluid samples at the specified sampling times from the fluid inlet to respective slots of the sensing unit.

In some embodiments the molecule sensor may comprise a sorbtive material adapted to retain the organic molecules.

The valve system may comprise a single valve positioned on the upstream side of the cartridge or a double valve positioned on a downstream and the upstream sides of the cartridge on either side of one of said slots.

The sensor may further comprise a transport mechanism for moving the valve system relative to successive slots The transport mechanism may include a threaded base.

The valve system may comprise one or more valve arrays.

The organic molecules may be hydrocarbon molecules.

The molecule sensors may be removable from the cartridge.

The sensor may further comprise a controller and a memory in communication with the controller, wherein the controller controls a relative position of the sequence of slots with respect to the valve system, and controls operation of the valve system. The memory may store log data associated with respective slots of the sensing unit, the log data selected from the group consisting of: a location at which the respective fluid sample was taken, the specified sampling times, durations of sampling, an inferred fluid flow rate, and a measured temperature. The sensor may further comprise one or more flow meters measuring flow rate of the fluid samples through respective slots, and wherein the memory further stores said measured flow rate. The flow rate of the fluid samples through respective slots may consist of a passive flow rate resulting from movement of the organic-molecule sensor through the underwater environment and/or an active flow rate caused by operation of a flow controller.

In another aspect of the invention there is provided an underwater vehicle comprising: a vehicle body comprising a buoyancy controller adapted to vary the buoyancy of the vehicle to control motion of the vehicle through an underwater environment; a sampling system adapted to sequentially sample fluid from the underwater environment at specified sampling times resulting in a sample sequence; and a sensor arrangement comprising a plurality of molecule sensors adapted to sense organic molecules in each respective sample of the sample sequence.

In some embodiments the vehicle may further comprise a communication system for communicating with a remote command unit and/or an underwater positioning system.

The vehicle may further comprise an imaging system for image data collection.

The vehicle may further comprise one or more additional sensors selected from the group consisting of: temperature sensor, pressure sensor, attitude sensor, conductivity sensor, oxygen sensor, fluorometer and optical backscatter sensor.

The vehicle may further comprise a flow meter for measuring flow past the plurality of molecule sensors.

The sensor arrangement may be removable from the underwater vehicle.

The plurality of molecule sensors may be removable from the sensor arrangement.

Each of the plurality of molecule sensors may comprise a sorbtive material adapted to retain the organic molecules.

The sampling system may comprise: a fluid inlet on an upstream side of the sensor arrangement, and a valve system adapted to open and close successive slots of the sensor arrangement to provide fluid samples at specified sampling times to respective slots of the sensor arrangement.

The sensor arrangement may comprise: a cartridge having a sequence of slots, and each slot may be adapted to receive one of the plurality of molecule sensors.

The vehicle may further comprise a controller and a memory in communication with the controller, wherein the controller controls a relative position of the sampling system with respect to the plurality of molecule sensors, and controls operation of the sampling system. The memory may store log data associated with respective molecule sensors of the plurality of molecule sensors, the log data selected from the group consisting of: a location at which a respective fluid sample was taken, the respective specified sampling times, durations of sampling, an inferred or measured fluid flow rate, and a measured temperature.

In another aspect of the invention there is provided a distributed system for detecting organic molecules in an underwater environment, the system comprising: i) a remote command unit adapted to receive data from an underwater vehicle and to transmit commands to the underwater vehicle; and ii) wherein the underwater vehicle comprises: a sampling system adapted to sequentially sample fluid from an environment of the vehicle at specified sample times resulting in a sample sequence, a sensor arrangement comprising a plurality of molecule sensors adapted to sense organic molecules in each respective sample of the sample sequence, a communication system adapted to transmit data to and receive commands from the remote command unit, and a controller to control onboard navigation and said sequential sampling based on said received commands.

In some embodiments the system may further comprise an underwater positioning system and wherein the underwater vehicle further comprises a communication system for communicating with the underwater positioning system for determining a location of the underwater vehicle and/or tracking a target in the underwater environment.

The sensor arrangement may be removable from the underwater vehicle.

The plurality of molecule sensors may be removable from the sensor arrangement.

Each of the plurality of molecule sensors may comprise a sorbtive material adapted to retain the organic molecules.

The sampling system may comprise: a fluid inlet on an upstream side of the sensor arrangement, and a valve system adapted to open and close successive slots of the sensor arrangement to provide fluid samples at specified sampling times to respective slots of the sensor arrangement.

The sensor arrangement may comprise: a cartridge having a sequence of slots, and each slot may be adapted to receive one of the plurality of molecule sensors.

In another aspect of the invention there is provided a method for sensing organic molecules comprising: in an underwater environment: sequentially sampling fluid from the underwater environment to produce a sample sequence; exposing a sequence of molecule sensors to respective samples of the sample sequence; and measuring and logging log data associated with each of the respective samples.

In some embodiments the molecule sensors may comprise a sorbtive material adapted to retain the organic molecules.

The method may further comprise subsequent retrieval of the molecule sensors for analysis of the sequence of molecule sensors in view of the log data. The subsequent retrieval may comprise removing above water the molecule sensors from a segmented container housing the molecule sensors.

The sequentially sampling may comprise opening and closing successive slots of a cartridge that houses the sequence of molecule sensors.

The exposing may comprise providing a path of fluid from the underwater environment past successive ones of the sequence of molecule sensors.

The log data may be selected from the group consisting of: a location at which a respective fluid sample was taken, the respective specified sampling times, durations of sampling, an inferred or measured fluid flow rate, and a measured temperature.

In another aspect of the invention there is provided a method for sensing organic molecules comprising: deploying an underwater vehicle in an underwater environment, wherein a buoyancy controller varies the buoyancy of the underwater vehicle to control motion of the vehicle through the underwater environment; sequentially sampling fluid from the underwater environment at specified sampling times resulting in a sample sequence; and presenting samples to respective ones of a plurality of molecule sensors adapted to sense organic molecules in each respective sample of the sample sequence.

In some embodiments the method may further comprise measuring and logging log data associated with each of the respective samples in the sample sequence, the log data selected from the group consisting of: a location at which a respective fluid sample was taken, the respective specified sampling times, durations of sampling, an inferred or measured fluid flow rate, and a measured temperature.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

A description of the present invention is made with reference to specific embodiments thereof as illustrated in the appended drawings. The drawings depict only typical embodiments of the invention and therefore are not to be considered limiting of its scope.

DETAILED DESCRIPTION OF THE EMBODIMENTS

An underwater vehicle used in accordance with an embodiment of the present invention can be any suitable vehicle adapted to travel at an appropriate depth (e.g., 1,000-6,000 m) and adapted to carry a water sampling and sensor arrangement as described below.

1. Autonomous Underwater Vehicle

Figure 1:
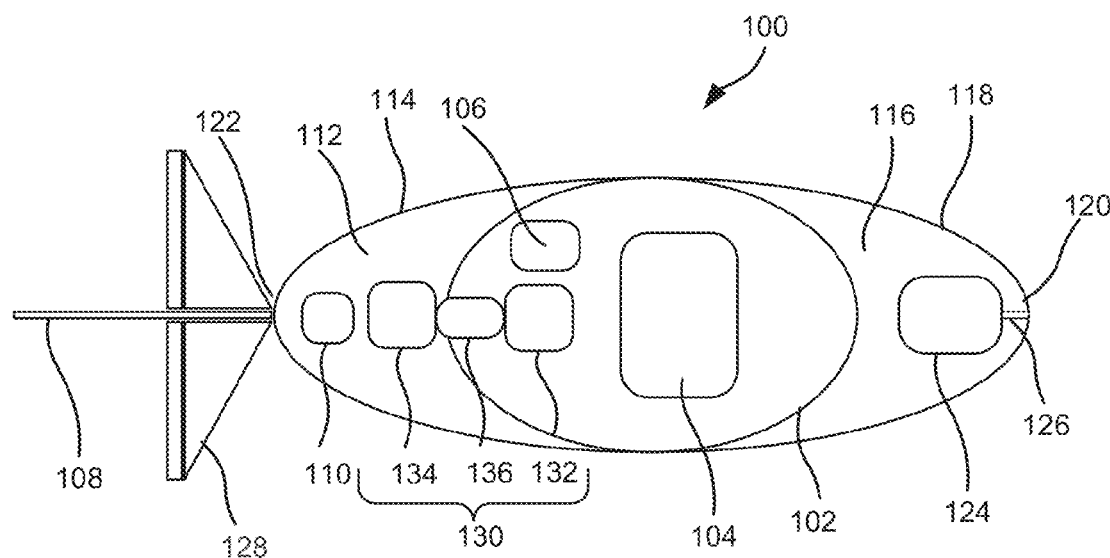
FIG. 1 is a schematic representation of an autonomous underwater vehicle (AUV).

In accordance with the embodiment shown in FIG. 1, the underwater vehicle is an autonomous underwater vehicle (AUV) 100, for example of the type described in U.S. Pat. No. 8,381,672 entitled "Systems and methods for compensating for compressibility and thermal expansion coefficient mismatch in buoyancy controlled underwater vehicles" which is hereby incorporated by reference.

The AUV 100 includes a pressure hull 102 that provides a sealed compartment, an aft cavity 112 formed by the aft fairing 114, and a forward cavity 116 formed by the forward fairing 118. Both the aft and forward cavities 112, 116 have a generally elliptical ogive shape or another suitable hydrodynamic shape.

The pressure hull 102 holds a double battery pack 104 and electronics 106. The electronics 106 includes a control unit for managing navigation and measurement components. The control unit includes components as appropriate, such as a processing device 200, discussed below with reference to FIG. 2.

The electronics 106 also includes data gathering devices such as a global positioning system (GPS), and sensors such as a temperature sensor and an attitude sensor that measures vehicle pitch, roll and magnetic heading. This type of AUV relies on power conservation to achieve long unmanned voyages (e.g., 6-9 months over 4,000-9,000 km). This is accomplished through, amongst others, the use of power control circuits and low-power circuitry. For example, low-power controllers are used together with various power switches to turn subsystems on and off.

The aft and forward cavities 112, 116 are at least partially filled with seawater that enters the AUV 100 at the nose 120 of the AUV 100 and flushes through to a vent (not shown) at the tail 122. Sensors that require contact with the surrounding environment can either be housed in the aft or forward cavity 112, 116, or can be positioned on a sensor fin (not shown), for example a dorsal sensor fin. One or more additional cavities may be provided as required. As shown in FIG. 1, in this embodiment a sensor 124 is positioned in the forward cavity 116, and the sensor 124 is in fluid communication with a fluid path 126 to the water inlet at the AUV nose 120.

Propulsion of the AUV 100 is provided by buoyancy control effected by variation of vehicle-displaced volume. This is accomplished by using a buoyancy control system 130 together with a compressibility compensation system 110. The buoyancy control system 130 includes an internal hydraulic reservoir 132, an external hydraulic accumulator 134, and a pump 136 configured to move liquid between the reservoir 132 and the accumulator 134. The compressibility compensation system 110, housed in the aft cavity 112 formed by the aft fairing 114, includes one or more compliant containers filled with a compressible liquid that gives the AUV 100 substantially the same compressibility as the surrounding seawater during operation by passively compensating for volume displacement differences.

Figure 2:
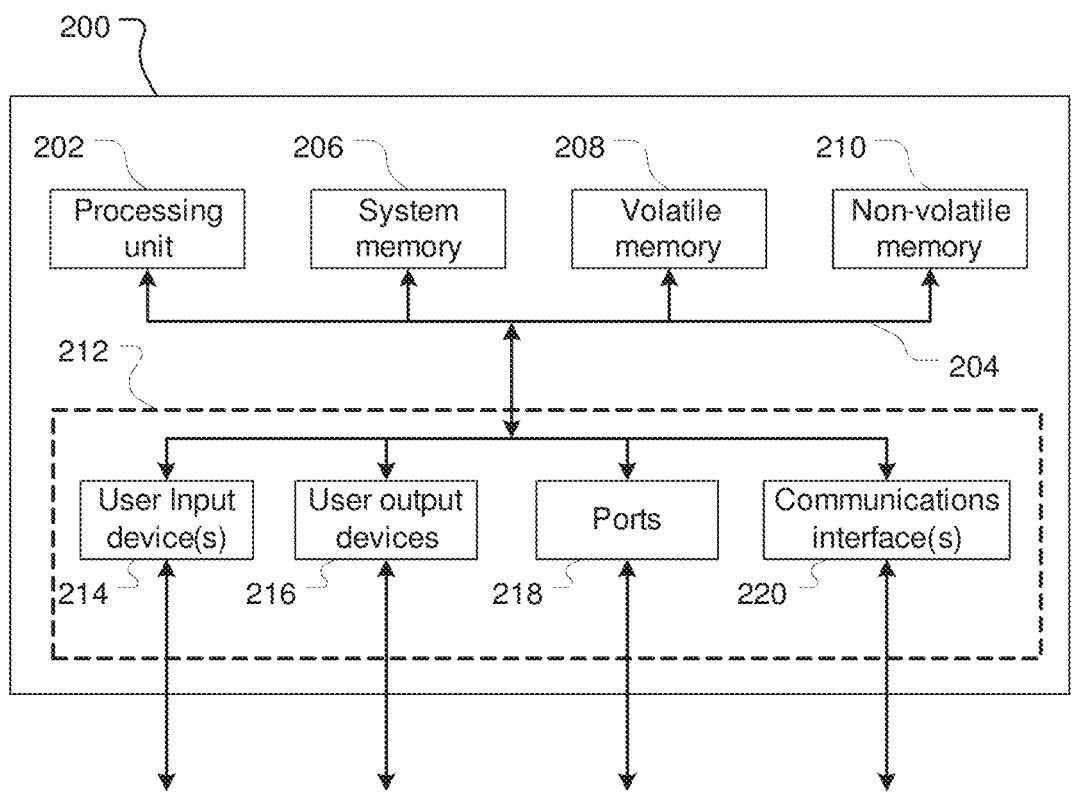
FIG. 2 is a schematic diagram of a processing device.

Referring to FIG. 2, processing device 200 includes a processing unit 202. The processing unit 202 may include a single processor (e.g., a microprocessor such as the Motorola MC68332, microcontroller, programmable logic controller (PLC), or other computational device), or may include a plurality of processors and/or controllers.

Through a communications bus 204 the processing unit 202 is in data communication with a system memory 206 (e.g., a BIOS), volatile memory 208 (e.g., random access memory including one or more DRAM modules or flash memory products), and/or non-volatile memory 210 (e.g., one or more hard disk drives, solid state drives). Instructions and data to control operation of the processing unit 202 are stored on the system, volatile, and/or non-volatile memory 206, 208, and 210.

The processing device 200 also includes one or more input/output interfaces (indicated generally by 212), which interface with a plurality of input/output devices. As will be appreciated, a wide variety of input/output devices may be used, including intelligent input/output devices having their own memory and/or processing units. By way of non-limiting example, the device 200 may include: one or more user input devices 214 (e.g., keyboard, mouse, a touch-screen, trackpad, microphone, etc.); one or more user output devices 216 (e.g., CRT display, LCD display, LED display, plasma display, touch screen, speaker, etc.); one or more ports 218 for interfacing with external devices such as drives and memory (e.g., USB ports, Firewire ports, eSata ports, serial ports, parallel ports, SD card port, Compact Flash port, etc.); and one or more communications interfaces 220 allowing for wired or wireless connection to a communications network (e.g., a Network Interface Card etc.). Some of these devices may be used before or after deployment of the vehicle for an unmanned underwater passage, but not included in the processing device 200 configuration underwater, e.g., a mouse, keyboard and/or display.

Communication with the communications network (and other devices connected thereto) is typically by the protocols set out in the layers of the OSI model of computer networking. For example, applications/software programs being executed by the processing unit 202 may communicate using one or more transport protocols, e.g., the Transmission Control Protocol (TCP, defined in RFC 793) or the User Datagram Protocol (UDP, defined in RFC 768).

The processing device 200 runs one or more applications to allow a user to operate the device 200. Such applications will typically include at least an operating system (such as Microsoft Windows®, Apple OSX, Apple iOS, Unix, Linux, Android, etc.).

Figure 3:
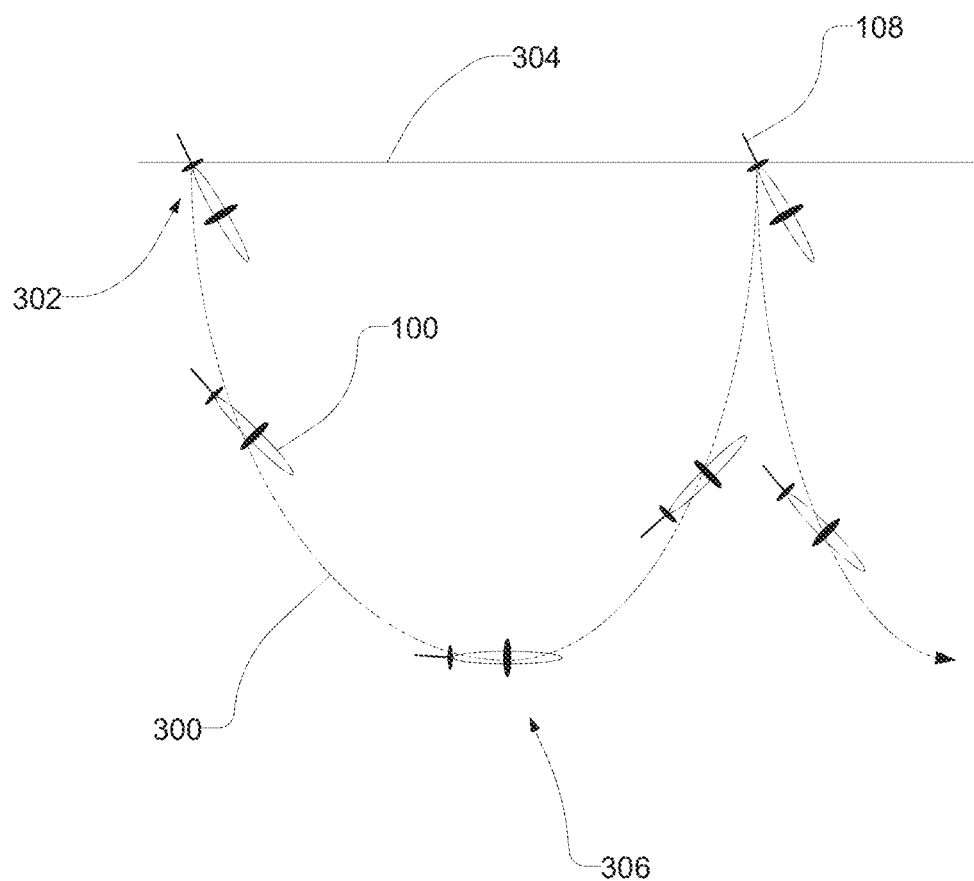
FIG. 3 is a schematic diagram of the movement of the AUV through the water.

To move along a selected trajectory, the AUV 100 dives and surfaces, executing a sawtooth path. FIG. 3 is a schematic diagram of the movement of the AUV 100 through the water as it alternately dives from the water surface 304 and descends and ascends along trajectory 300. The buoyancy control system 130 of the AUV 100 is configured to change the volume of the fixed mass AUV 100 to move the AUV along trajectory 300. At position 302, when the AUV 100 is at the water surface 304, the reservoir 132 is filled with oil to make the AUV 100 less buoyant in order to start a dive. Once the AUV 100 reaches its desired depth at position 306, the pump 136 moves the oil from the reservoir 132 to the external accumulator 134. This increases the AUV's volume displacement to make the AUV 100 more buoyant so it can ascend to the surface along trajectory 300. The AUV 100 continues moving through the water in this way, gaining speed as it dives and ascends. Attitude control is accomplished by moving mass within the AUV 100, for example the battery pack 104. Wings (not shown) provide hydrodynamic lift to propel the AUV 100 forward as it sinks or rises. The AUV 100 also has a rudder 128. The typical speed that an AUV travels is 0.1-0.5 m/s, typically 0.2 m/s (which is about 12 nautical miles per day).

The AUV 100 does not need to reach the surface on each ascent, and is able to travel diving and ascending within a depth range below the surface, for example between 600 and 1000 m below the ocean surface. In some instances not surfacing may be preferable, for example because stronger ocean currents tend to impact the AUV's movement closer to the surface (e.g., in the upper 100 to 400 m below the ocean surface) than at a greater depth where the currents are typically weaker.

When the AUV 100 is at the water surface, it dips its nose 120 so that the antenna 108 is above water. The antenna 108 typically includes both a GPS antenna and a wireless modem antenna. Each time the AUV 100 surfaces, the AUV 100 is able to update its position via the GPS instrumentation. The AUV 100 uploads data, for example log data and sensor data, via the modem antenna. The AUV 100 also receives data via the modem antenna when the AUV 100 is at the water surface 304, for example navigation or other operational commands.

A remote command unit communicates with the AUV 100 via a wireless or satellite link when the AUV surfaces. The remote command unit may include one or more processing devices, for example as described above with reference to FIG. 2, and transmits operational and navigational control signals to the AUV 100 via its input/output interface. The remote command unit receives and stores the log, sensor and updated position data from the AUV 100.

As the log and sensor data is uploaded periodically when the AUV surfaces, this data may be used to influence the AUV trajectory and/or sampling parameters during the AUV's passage. The remote command unit analyses the log and sensor data and based on this transmits updated operational and navigational control signals to the AUV. For example, the number of samples and/or sampling duration may be increased where an increased temperature has been measured if the temperature increase could relate to thermogenic hydrocarbons.

In some embodiments the remote command unit may be based on the vessel that launches the AUV, or on another vessel. In other embodiments the remote command unit may be land based. In some embodiments data analysis and subsequent determination of operational and/or navigational control signals may be performed or partially performed by an operator.

In some embodiments, the underwater vehicle can be a remotely operated underwater vehicle (ROV).

Using an AUV for exploration or for detecting hydrocarbons presents a number of challenges. Although configurable, there are limitations on the AUV's payload with respect to at least size, weight and power requirements. Also, using GPS technology, the location of an AUV is only accurately determined when the AUV surfaces and GPS coordinates can be determined 2. Sensor Arrangement Typical sensors used on AUVs include a conductivity and temperature sensor pair, a pressure sensor and altimeter transducer to measure seawater properties and stratification. Typical additional sensors for oceanography include an oxygen sensor, an optical backscatter sensor, and a chlorophyll fluorometer. The sensor data derived from these and/or any other sensors is stored in the onboard memory, and then the sensor data is uploaded to the remote command unit, e.g., via a wireless or satellite uplink when the AUV surfaces.

Temperature sensors can be useful for detecting thermogenic hydrocarbons, for example as applicable for detecting thermal insulation damage to sea bottom infrastructure or pipelines. However, more accurate hydrocarbon sensing (for example using spectrometry, chromatography or PAH fluorometry) is challenging with an AUV due at least to the payload and power limitations associated with AUVs.

A solution described herein is to sequentially sample the fluid that the AUV is moving through, sensing a molecule concentration in each sample (e.g., a hydrocarbon concentration), and then to recover and analyse the sensed molecule concentration after the AUV's run. A series of samples is taken along with associated log data for example from other onboard sensors. Log data may include one or more of the following: the time that the sample of was taken, the duration of the sample, the flow rate of the fluid during sampling (inferred and/or measured), the date of sampling, the location of sampling and temperature data per sample.

As with other sensor data, during the AUV's passage the log data is stored in the onboard memory, and then the uploaded to the remote command unit.

Figure 4:
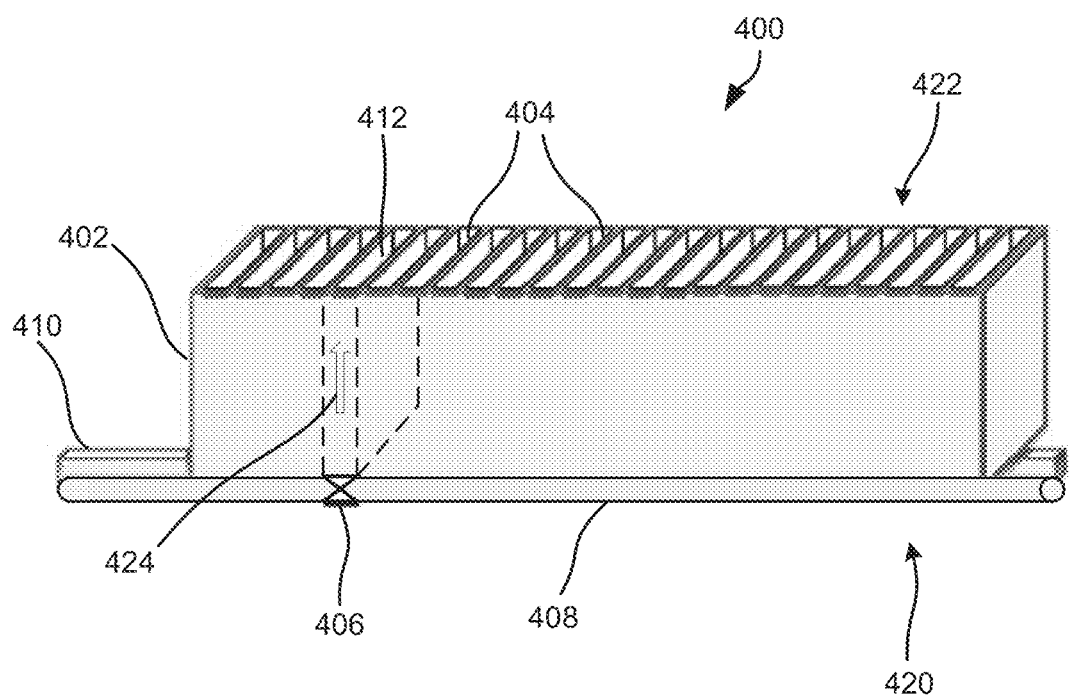
FIG. 4 is a diagrammatic representation of a hydrocarbon sampling device.

FIG. 4 shows a diagram of an organic molecule sensing unit 400. The sensing unit 400 includes a segmented container in the form of cartridge 402 with a sequence of slots 404. Each slot 404 contains a molecule sensor that includes a sorbtive material, e.g., one or more removable discs (not shown) that have a sorbtive organic coating, adapted to retain organic molecules (such as hydrocarbons) from water that flows through the slots 404. Sequential exposure of the discs in order to sense hydrocarbons in an underwater environment at specified time intervals produces a sequenced sensed molecule (e.g., hydrocarbon) set along the AUV's path.

Water flows through the slots 404 in the direction indicated by arrow 424 so that the sensing unit 400 has a downstream surface 422 and an upstream surface 420.

Cartridge shape and size are flexible and may be configured based on aspects of a particular sampling run. For example a cartridge may be shaped to maximise the number of samples and to fit within the physical constraints of the AUV, or to minimise/maximise the volume and/or retention time of liquid in contact with the discs. The number of slots in the cartridge depends on various factors including but not limited to weight/size/power limitations on the AUV payload, what type of molecules are being sampled, and/or the planned time/distance of the AUV expedition. For example, for a sampling device placed in a forward cavity with a central length of approximately 20 cm, a single straight cartridge with 1 mm spaced slots can have up to 400 slots. However, the size, shape and position of the cartridge, slots and discs are all configurable, and therefore in different configurations, the sampling device can have between 100 and 1000 slots, between 1000 and 4000 slots, or more than 5000 slots.

A movable valve 406 is used to control the flow of water through successive slots 404. The movable valve 406 is positioned on a transport mechanism 408 (for example a threaded shaft) on the upstream surface 420 of the sensing unit 400, the transport mechanism and valve 406 being controlled by one or more controllers, e.g., included in the electronics 106 in the pressure hull 102. In other arrangements a separate controller may be provided to control operation of the sensing unit 400, and this controller may include memory used for storing control parameters and/or sampling parameters such as the time and/or duration of sampling. This memory may also be used for storing log data as described above.

When the movable valve 406 opens adjacent a specific slot, water flows from a water inlet 410 through the valve 406 and then through an opened slot 412 for a specified sample time during which organic molecules, e.g., hydrocarbons, are sensed by the molecule sensor, for example by being captured on that slot's sorbtive disc. The sample time is configurable, for example to suit the specific application (what is being sampled under which circumstances), and may depend on a number of factors including and not limited to the speed that the AUV is travelling at, the type of organic molecules being sampled, an estimated concentration of organic molecules in the water and/or the flow rate through the slot 412. For example, sampling times may be increased to reduce the number of total samples or to produce a single composite sample over a larger area. Alternatively, sampling times may be reduced to increase the sampling resolution over a smaller area.

For example, the sample time may be between 1 and 5 seconds, or between 5 and 10 seconds. Likewise, the time between successive samples depends on, for example, the sawtooth movement of the AUV, the speed of the AUV and the topography of the area. The time between samples may be, for example equal to the sample time to provide continuous sampling, or may be larger, for example between 10 and 20 seconds, or between 1 and 5 minutes. The sample time may be the same or different for different slots/samples. Likewise, the time between samples may be the same or different for different slots/samples.

In some embodiments the water inlet 410 receives water from a fluid path 126 at the AUV nose 120, for example where the sensing unit 400 is deployed in the forward cavity 116 of the AUV. Alternatively, if the sensing unit 400 is deployed on a sensor fin, the water inlet 410 may receive a water supply from the outside environment through a device packaging, e.g., via a venturi tube.

An average water flow rate through the opened slot 412 may be inferred, for example in view of the speed of the AUV (referred to herein as the passive flow rate). The inferred flow rate is determined by the sensing unit's controller and stored on the controller's memory together with the log data for respective samples. Alternatively the water inlet 410 may include a flow controller for actively controlling the water flow rate by pumping water through the sensing unit 400 and/or one or more flow meters (not shown) that may be positioned in inlet 410 to measure passive (due to AUV movement) and/or active (due to the operation of a flow controller) flow rate. The water flow per sample period is logged. The sample represents an average over the path traveled by the AUV during the sample time, and the flow rate is used to calculate the average concentration.

In some embodiments the downstream surface 422 of the sensing unit 400 includes a cover assembly (not shown). The cover assembly includes a water outlet to enable removal of water that has passed through the opened slot 412. In some embodiments the water outlet is an outlet manifold along the downstream surface of the sampling device.

In some embodiments the movable valve 406 is a valve pair, with a first valve at the upstream surface 420 and a second valve at the downstream surface 422, the valve pair moved together by the transport mechanism. The second valve facilitates the flow of water away from the opened slot 412 and through the water outlet (not shown).

In some embodiments one or more valve arrays are used instead of or in addition to one or move movable valves. In some embodiments the valve(s) or valve array is stationary while the cartridge is moved by a transport mechanism.

When the AUV completes its journey and is recovered, the cartridge is recovered and the discs are analysed e.g., for quantification of hydrocarbon concentration as well as general fingerprinting, for example using laboratory gas chromatography flame ionisation detection (GC FID). Data obtained from the samples is correlated to the log data as well as any other sensor data so that, for example, hydrocarbon concentrations can be correlated with time, position and temperature information.

In some embodiments, other types of data collection are done such as image data collection, e.g., using an imaging system that includes one or more types of video or still photography, for example ultraviolet, infrared, visible spectrum (supplemented with a flash) and sonar. For leak detection along pipelines, images collected in this way provide another means to detect a leak. For exploration the images can be used to identify, for example, structures or environmentally sensitive habitats (e.g., deep ocean coral) associated with vents or hydrocarbon seeps. Image data is transmitted when the AUV surfaces.

3. Location and Navigation

Because the AUV is only able to determine its location via GPS when it surfaces, accurate underwater positioning may be assisted by an additional underwater positioning system.

Figure 5A:
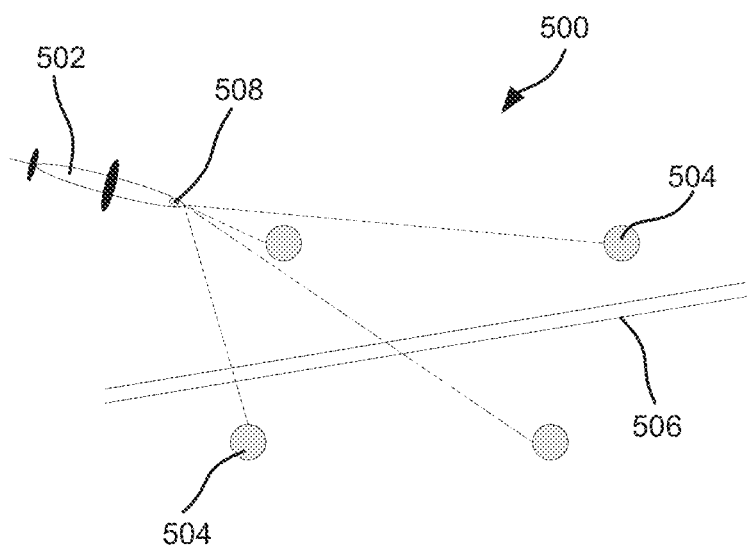
FIG. 5A is a schematic representation of long baseline underwater acoustic positioning.

FIG. 5A shows a long baseline (LBL) underwater acoustic positioning system 500 used to accurately determine the position of the AUV 502. A seafloor baseline transponder network including several transponders 504 is set up across the area of operation, in this case an area around pipeline 506. The relative positions of the transponders 504 are known. An interrogator 508 mounted in the AUV 502 transmits an acoustic signal that is received by the baseline transponders 504. The replies from the transponders 504 received by the interrogator 508 enable the AUV 502 to accurately determine its position in order to aid its navigation and/or accurately log its position. The LBL system 500 may be more appropriate for exploration applications.

Figure 5B:
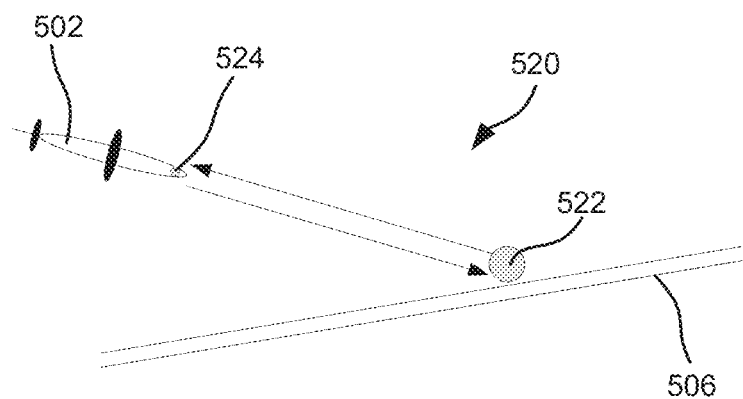
FIG. 5B is a schematic representation of inverted ultra short baseline positioning.

FIG. 5B shows an inverted ultra short baseline (iUSBL) positioning system 520. A simpler though less accurate system than LBL, the iUSBL system 520 includes only one or more target transponders 522 instead of a large array of baseline transponders. The AUV 502 carries transceiver 524 that locates the transponder(s) for target tracking, for example where one or more positions along pipeline 506 are targeted. The iUSBL system 520 may be more appropriate for infrastructure tracking applications.

Using AUVs for sensing organic molecules, for example for detecting underwater hydrocarbons, has a number of advantages. AUVs are relatively low-cost vehicles (as compared to ROVs, for example) so that loss or damage of an AUV gathering data and measurements is not as costly as the loss of another type of vehicle could be. AUVs are also relatively small and light so that a small surface vessel with a limited crew is able to deploy multiple AUVs for efficient execution of large surveys.

Notwithstanding that the present invention has been described above in terms of alternative embodiments, it is anticipated that still other alterations, modifications and applications will become apparent to those skilled in the art after having read this disclosure. For example, it is to be understood that the present invention contemplates that, to the extent possible, one or more features of any embodiment can be combined with one or more features of any other embodiment. It is therefore intended that such disclosure be considered illustrative and not limiting, and that the appended claims be interpreted to include all such applications, alterations, modifications and embodiments as fall within the true spirit and scope of the invention.

The invention claimed is:

1. A sensor comprising:
   i) a sensing unit comprising:
      a cartridge having a sequence of slots, and
      a molecule sensor in each slot for sensing organic molecules; and
   ii) a sampling system adapted to sequentially sample fluid from an underwater environment at specified sampling times, the sampling system comprising:
      a fluid inlet on an upstream side of the sensing unit, and
      a valve system adapted to open and close successive slots in the cartridge to provide fluid samples at the specified sampling times from the fluid inlet to respective slots of the sensing unit.

2. The sensor of claim 1, wherein the molecule sensor comprises a sorbtive material adapted to retain the organic molecules.

3. The sensor of claim 1, wherein the valve system comprises a single valve positioned on the upstream side of the cartridge or a double valve positioned on a downstream and the upstream sides of the cartridge on either side of one of said slots.

4. The sensor of claim 1, further comprising a transport mechanism for moving the valve system relative to successive slots.

5. The sensor of claim 1, wherein the transport mechanism includes a threaded base.

6. The sensor of claim 1, wherein the valve system comprises one or more valve arrays.

7. The sensor of claim 1, wherein the organic molecules are hydrocarbon molecules.

8. The sensor of claim 1, wherein said molecule sensors are removable from the cartridge.

9. The sensor of claim 1, further comprising a controller and a memory in communication with the controller, wherein the controller controls a relative position of the sequence of slots with respect to the valve system, and controls operation of the valve system.

10. The sensor of claim 9, wherein the memory stores log data associated with respective slots of the sensing unit, the log data selected from the group consisting of: a location at which the respective fluid sample was taken, the specified sampling times, durations of sampling, an inferred fluid flow rate, and a measured temperature.

11. The sensor of claim 10, further comprising one or more flow meters measuring flow rate of the fluid samples through respective slots, and wherein the memory further stores said measured flow rate.

12. The sensor of claim 11, wherein said flow rate of the fluid samples through respective slots consists of a passive flow rate resulting from movement of the organic-molecule sensor through the underwater environment and/or an active flow rate caused by operation of a flow controller.

* * * * *